(12) United States Patent
Campbell et al.

(10) Patent No.: US 9,028,444 B2
(45) Date of Patent: May 12, 2015

(54) PIVOTING RING SEAL

(75) Inventors: Carey V. Campbell, Flagstaff, AZ (US); Nathan L. Friedman, Flagstaff, AZ (US); Benjamin M. Trapp, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 174 days.

(21) Appl. No.: 13/446,915

(22) Filed: Apr. 13, 2012

(65) Prior Publication Data

US 2012/0277718 A1 Nov. 1, 2012

Related U.S. Application Data

(60) Provisional application No. 61/475,822, filed on Apr. 15, 2011.

(51) Int. Cl.
*A61M 25/10* (2013.01)

(52) U.S. Cl.
CPC .......... *A61M 25/10* (2013.01); *A61M 25/1018* (2013.01); *A61M 2025/1068* (2013.01); *A61M 2025/1084* (2013.01)

(58) Field of Classification Search
CPC ............ A61M 25/10; A61M 2025/1093; A61M 2025/1081; A61M 2025/1084; A61M 25/1034; A61M 25/0074; A61M 25/1029; A61M 2025/0059; A61M 2025/1059; A61M 25/1018

USPC .......... 604/95.03, 96.01, 99.01, 103, 103.03, 604/103.06, 103.08, 103.09, 915

See application file for complete search history.

(56) References Cited

U.S. PATENT DOCUMENTS

| | | | |
|---|---|---|---|
| 4,349,033 A | 9/1982 | Eden | |
| 5,102,402 A * | 4/1992 | Dror et al. | 604/265 |
| 5,246,421 A | 9/1993 | Saab | |
| 5,520,646 A | 5/1996 | Andrea | |
| 5,556,413 A | 9/1996 | Lam | |
| 6,537,247 B2 * | 3/2003 | Shannon | 604/103.05 |
| 6,623,451 B2 * | 9/2003 | Vigil | 604/99.01 |

FOREIGN PATENT DOCUMENTS

| | | |
|---|---|---|
| CN | 201217091 | 4/2009 |
| FR | 2806016 | 9/2001 |
| WO | 96/40349 | 12/1996 |
| WO | 2007/095125 | 8/2007 |

\* cited by examiner

*Primary Examiner* — Rebecca E. Eisenberg
(74) *Attorney, Agent, or Firm* — David J. Johns

(57) ABSTRACT

The instant invention provides for a pivoting ring that can be used as a seal for an inflatable member. The pivoting ring seal offers a mechanical action which acts to tighten with increasing inflation and/or expansion of an inflatable member. As the inflatable member increases in pressure and/or size, one side of the ring is lifted and pivots around a fulcrum in the middle of the ring seal causing the opposite side of the ring seal to decrease in diameter. The pivot ring causes the opposite part of the seal to tighten about an inner member allowing for a higher-pressure seal. In addition to a higher pressure seal, the working length of the inflatable member can be adjusted by moving the ring along the length of the inflatable member.

50 Claims, 12 Drawing Sheets

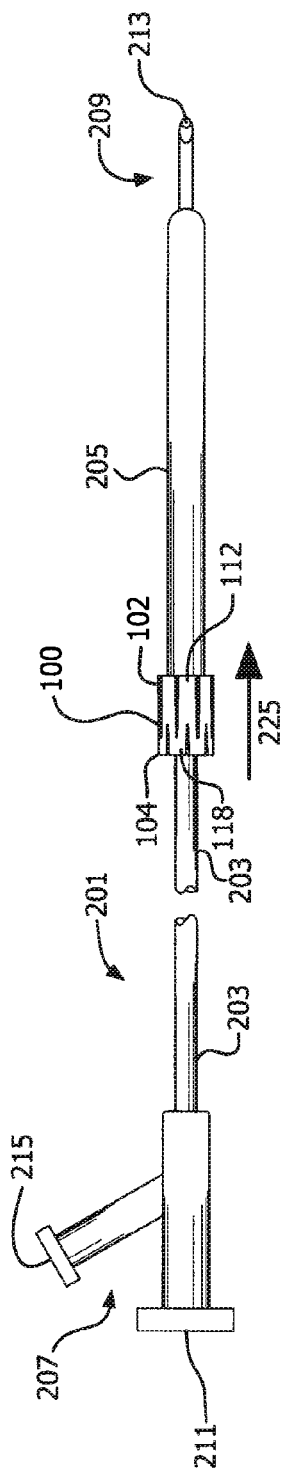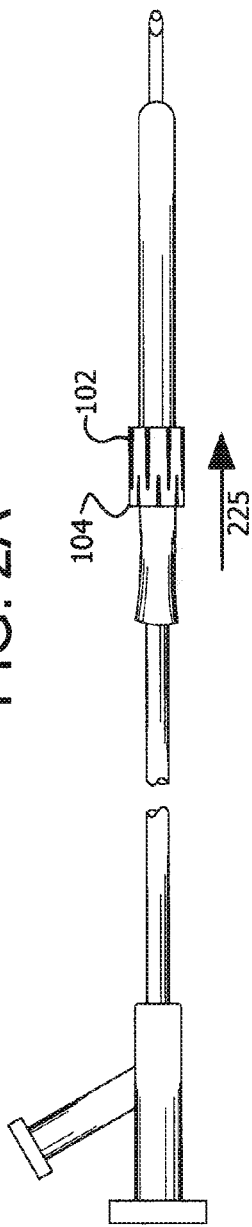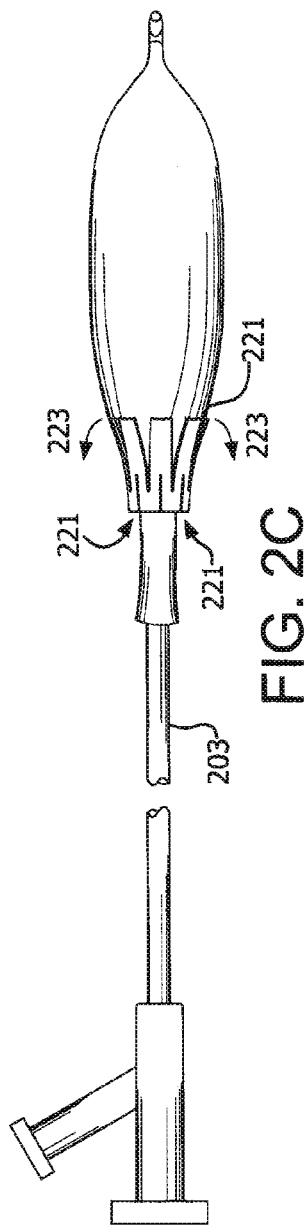

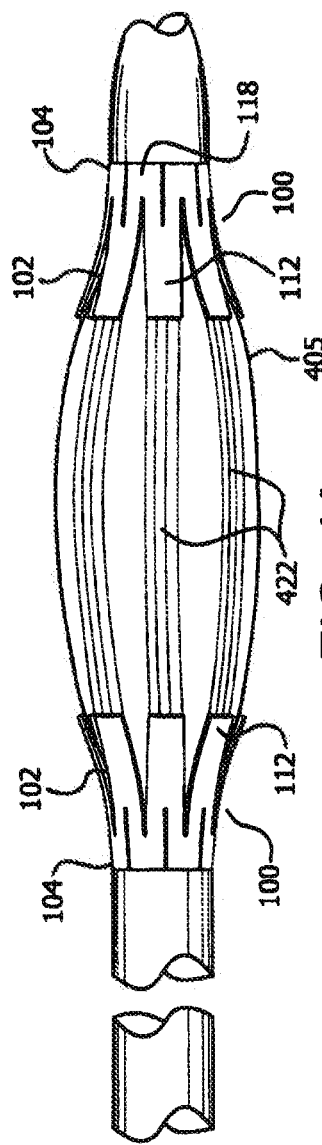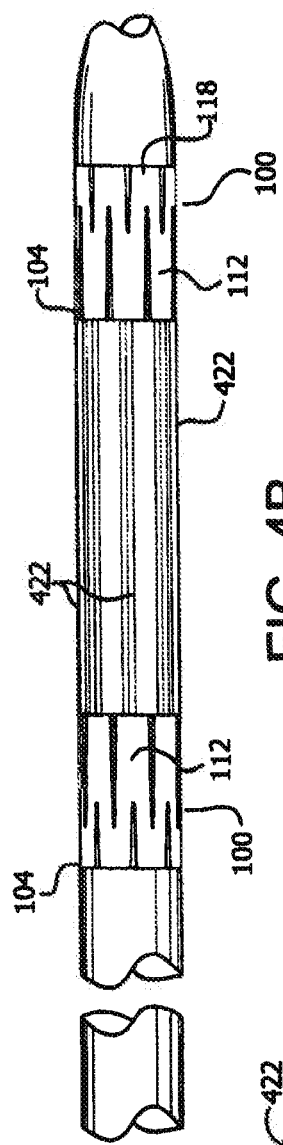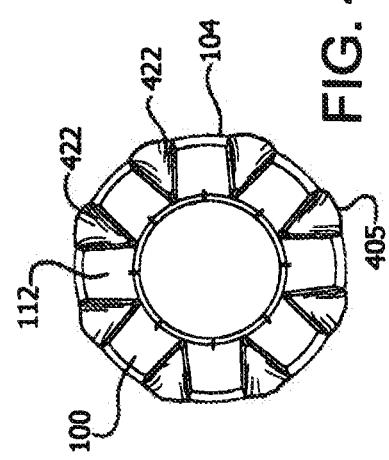

PIVOTING RING SEAL

CROSS-REFERENCE TO RELATED APPLICATIONS

This application claims the priority benefit under 35 U.S.C. 119(e) of U.S. Provisional Application No. 61/475,822 filed on Apr. 15, 2011 which is incorporated by reference herein in its entirety.

BACKGROUND OF THE INVENTION

There are many medical procedures which employ balloon catheters. In most cases, the length of the balloon must be pre-determined by the clinician prior to selection and insertion of the balloon catheter into the body. For example, in balloon angioplasty, the length of the diseased blood vessel is first determined. Usually, the physician determines in advance the approximate size of the vessel area to be treated. This can be done, for example, through fluoroscopic X-ray, ultrasound imaging, and/or CAT scanning techniques. When balloon length choices are few, a clinician will generally choose a length shorter than the length of the lesion to be treated and will sequentially dilate different portions of the vessel. This extends the time and risks of the procedure. Where several catheters of differing balloon lengths are available the physician will select a balloon length which will cover the entire length of the portion of the vessel requiring dilatation. If two or more blockage sites of different lengths exist within the same artery and the physician determines that two or more different sized balloons must be used, the physician will generally treat the most proximal site first, deflate and withdraw the first balloon catheter, and then insert a second balloon catheter with a different length balloon to treat the second stenotic region. Shorter balloons are often used to dilate lesions located on sharp bends in coronary arteries to prevent straightening and possible damage during the dilatation procedure. Longer balloons are employed to dilate large areas with extensive disease. Changing balloons, however, is a costly, time-consuming and potentially risky procedure that could lead to injury or death of the patient.

In addition, while it is believed the primary use for balloon catheters is for treating profuse disease in blood vessels, and in particular diseased portions of peripheral and coronary arteries, there are certain other procedures where one of a plurality of catheters having different length balloons must be selected. For example, when utilizing a drug eluting balloon, it would be preferable to determine the area of the vessel where a drug is to be delivered and adjust the balloon length accordingly. This will only release the drug in the targeted area and avoid exposing healthy portions of the vessel to the drug. Usually these drugs are toxic to healthy tissue so a targeted approach is desirable.

In addition, what has been needed and heretofore unavailable is a stent delivery device, which allows for a variable length expandable member needed for proper stent deployment and safe and effective sizing of a deployed stent.

Thus, in the foregoing procedures, the physician must have catheters with various sized balloons on hand so that he/she can select the proper size balloon when performing the procedure.

The instant invention obviates the need for having multiple length balloons in a stock room, allows for customizing the length of a balloon to the size of a lesion or stent and provides for targeted delivery of a drug utilizing a drug eluting balloon.

SUMMARY OF THE INVENTION

Compared to traditional balloon seals requiring adhesives and/or crimped bands to prevent leakage or failure of an inflatable member, the ring seal of the invention (i.e. the ring of the invention, also sometimes referred to herein as band(s), ring member(s) and pivot ring(s)) offers a mechanical action which acts to tighten the seal with increasing inflation and/or expansion. As the inflatable member increases in size, one side of the ring is lifted and pivots around a fulcrum between the ends of the ring seal causing the opposite side of the ring seal to decrease in diameter and/or exert a compressive force. The pivoting (and the reduction in diameter) causes the opposite part of the seal to tighten about an inner member allowing for a higher-pressure seal. In addition to a higher pressure seal, the working length of the inflatable member can be adjusted by moving the ring seal along the length of the inflatable member while it is not inflated.

Thus, one embodiment of the invention is directed to a medical device comprising an inflatable member wherein the working length of the inflatable member is adjustable in situ and/or by medical personnel before insertion into a body conduit. Significant benefits can result from this unique adjustability, again whether through the ability of clinicians to adjust the working length of an inflatable member in situ during a medical procedure, by adjusting the size of the inflatable member prior to performing a medical procedure, or some combination of the two.

Another embodiment of the invention comprises a seal that increases its sealing force as pressure and size of an inflatable member increases.

Another embodiment of the invention comprises a medical device comprising an inflatable member having opposing ends, a smaller deflated profile and a larger inflated profile, a working length, and a ring member having opposing ends, said ring member being slidable, whether in situ or prior to insertion of a device in the body, or some combination, to any position between the opposing ends of the deflated inflatable member, wherein when one opposing end of said ring member increases in diameter, the other opposing end of said ring member decreases in diameter upon inflation of the inflatable member. In one embodiment, the inflatable member drives the increase in the diameter of the ring member in one opposing end. In another embodiment, the decrease in diameter of one opposing end of said ring member restricts inflation of a portion of said inflatable member.

In another embodiment, said inflatable member is disposed over an elongate member. In another embodiment, said elongate member is a catheter or a guidewire. In another embodiment, the decrease in diameter of the opposing end of said ring member makes said end constrict about said inflatable member and/or said elongate member. In another embodiment, the constriction of the opposing end of said ring member against said inflatable member and/or said elongate member results in a seal of at least one end of said inflatable member. In another embodiment, as the diameter of an opposing end of said ring member decreases, it further constricts against said inflatable member and/or said elongate member resulting in a tighter seal of at least one end of said inflatable member. In another embodiment, the decrease in diameter of one of the opposing ends of said ring member restricts axial movement of said ring member. In another embodiment, said inflatable member is a medical balloon. In another embodiment, said medical balloon comprises expanded polytetrafluoroethylene (ePTFE). In another embodiment, the position of said ring member adjusts the working length of said medical balloon. In another embodiment, one method of adjusting the position of the ring member is by sliding the ring member along the axis of said medical balloon to the appropriate location in said inflatable member. In another embodiment, said medical balloon further comprises a balloon cover.

In another embodiment, said balloon cover comprises ePTFE. In another embodiment, said medical balloon comprises a drug coating on said balloon and/or balloon cover. In another embodiment, said ring member comprises a resilient metal. In another embodiment, said resilient metal is nitinol. In another embodiment, the position of said ring member adjusts the working length of the expandable portion of said inflatable member.

Another embodiment of the invention comprises a medical device comprising an inflatable member having opposing ends, a smaller deflated profile and a larger inflated profile, a working length, and a ring member having opposing ends, wherein said ring member is positioned between the opposing ends of the said inflatable member and wherein an increase in diameter on one of the opposing ends of said ring member results in a compressive force in the other opposing end of said ring member. In one embodiment, said inflatable member drives the increase in the diameter of said ring member in one opposing end. In another embodiment, said compressive force is caused by an increase in diameter of one of the opposing end of said ring member. In another embodiment, said compressive force of one of said opposing end of said ring member restricts axial movement of said ring member. In another embodiment, said compressive force of one of said opposing end of said ring member restricts inflation of a portion of said inflatable member. In another embodiment, said inflatable member is disposed over an elongate member. In another embodiment, said elongate member is a catheter or a guidewire. In another embodiment, said compressive force causes said opposing end of said ring member to constrict against said inflatable member and/or said elongate member. In another embodiment, as the diameter of said opposing end of said ring member decreases, it further constricts against said inflatable member and/or said elongate member resulting in a tighter seal of at least one end of said inflatable member. In another embodiment, the inflatable member is a medical balloon. In another embodiment, said medical balloon comprises ePTFE. In another embodiment, the position said ring member adjusts the working length of said medical balloon. In another embodiment, said medical balloon further comprises a balloon cover. In another embodiment, said balloon cover comprises ePTFE. In another embodiment, said medical balloon comprises a drug coating on said balloon and/or balloon cover. In another embodiment, said ring member comprises a resilient metal. In another embodiment, said resilient metal is nitinol.

Another embodiment of the invention comprises a method of adjusting the working length of an inflatable member comprising disposing at least one ring member onto an inflatable member having a length, said ring member configured to have opposing ends whereby when one opposing end of said ring member increases in diameter upon inflation of an inflatable member the other opposing end of said ring member decreases, and sliding the at least one ring member to a predetermined position along the length of said inflation member,. In one embodiment, increasing the diameter of one of the opposing ends of said ring member results in a compressing force in the other opposing end of said ring member. In another embodiment, said inflatable member drives the increase in the diameter of said one opposing end of said ring member. In another embodiment, there may be two or more ring members disposed on said inflatable member. In another embodiment, the decrease in diameter of said one opposing end of said ring member restricts inflation of a portion of said inflatable member. In another embodiment, said inflatable member is disposed over an elongate member. In another embodiment, said elongate member is a catheter or a guidewire. In another embodiment, the decrease in diameter of the opposing end of said ring member makes said end constrict against the inflatable member and the elongate member. In another embodiment, the constriction of the opposing end of said ring member against said inflatable member and/or said elongate member result in a seal of at least one end of said inflatable member. In another embodiment, as the diameter of the opposing end of said ring member decreases, it further constricts against said inflatable member and/or said elongate member resulting in a tighter seal of at least one end of said inflatable member. In another embodiment, the decrease in diameter of one of said opposing end of said ring member restricts axial movement of said ring member. In another embodiment, said inflatable member is a medical balloon. In another embodiment, said medical balloon comprises ePTFE. In another embodiment, said medical balloon further comprises a balloon cover. In another embodiment, said balloon cover comprises ePTFE. In another embodiment, said medical balloon comprises a drug coating on said balloon and/or balloon cover. In another embodiment, said ring member comprises a resilient metal. In another embodiment, said resilient metal is nitinol.

Another embodiment of the invention comprises a method of introducing a customizable stent into a body conduit comprising, providing a customizable stent and a medical balloon having opposing ends, a smaller deflated profile and a larger inflated profile, and a working length, adjusting said customizable stent to a predetermined length, adjusting said working length of said medical balloon by disposing and sliding at least one ring member between said opposing ends of said medical balloon, wherein said ring member comprises opposing ends and an increase in diameter on one of the opposing ends of said ring member results in a compressing force in the other opposing end of said ring member, disposing said stent onto the working length of the medical balloon, and inserting said medical balloon, at least one ring member and stent into a body conduit. In one embodiment, said medical balloon and said stent are delivered to a predetermined site within said body conduit and said working length of said medical balloon is expanded thereby delivering said stent disposed on said balloon. In another embodiment, said customizable stent comprises stent rings interconnected by polymer webs. In another embodiment, said customizable stent is customized by cutting said polymer webs interconnecting said stent rings and removing said stent rings. In another embodiment, said method comprises using two ring members and sliding said ring members to adjust the working length of said medical balloon. In another embodiment, said medical balloon is disposed over an elongate member. In another embodiment, said elongate member is a catheter. In another embodiment, said medical balloon comprises ePTFE. In another embodiment, said medical balloon further comprises a balloon cover. In another embodiment, said balloon cover comprises ePTFE. In another embodiment, said medical balloon comprises a drug coating on said balloon and/or balloon cover. In another embodiment, said ring member comprises a resilient metal. In another embodiment, a suitable resilient metal is nitinol.

Another embodiment of the invention comprises a pivoting ring that comprises a first end and second end, wherein when the first end increases in diameter the second end decreases in diameter. In one embodiment, said ring comprises a resilient material. In another embodiment, said resilient material is selected from the group consisting of a metal and polymer. In another embodiment, said metal is nitinol.

BRIEF DESCRIPTION OF THE DRAWINGS

The exemplary embodiments of the present invention will be described in conjunction with the accompanying drawings. The accompanying drawings are included to provide a further understanding of the invention and are incorporated in and constitute a part of this specification, illustrate embodiments of the invention and together with the description serve to explain the principles of the invention.

FIG. 1A depicts a side view of the closed ring and FIG. 1B depicts the end view of the closed ring.

FIG. 1C depicts a side view of an open ring and FIG. 1D depicts the end view of the open ring.

FIGS. 2A and 2B depict one use of the ring of the invention placed over a balloon catheter. FIGS. 2A and 2B depicted the balloon catheter with the non-inflated balloon and the ring of the invention placed over the balloon.

FIG. 2C depicts an expanded balloon with the ring of the invention in an open configuration.

FIGS. 4A, 4B and 4C depict a side view and an end view (4C) of a balloon with two pivot rings which help refold a balloon after inflation.

DETAILED DESCRIPTION OF THE ILLUSTRATED EMBODIMENTS

Compared to traditional seals requiring adhesives and/or crimped bands to prevent failure of an inflatable member, the pivot ring seal of the invention (i.e. the ring of the invention) offers a mechanical action which acts to tighten the seal with increasing expansion and/or inflation (which results in an increase in pressure). As the inflatable member increases in pressure and/or size, one side of the ring is lifted and pivots the opposite side of the ring seal around a fulcrum between the ends of the ring seal. The pivoting causes the opposite part of the seal to tighten about an inner member allowing for a higher-pressure seal. In addition to a higher-pressure seal, the working length of the inflatable member can be adjusted by moving the ring seal along the length of the inflatable member prior to inflation and/or after inflation and deflation. As used herein the term "working length" is the length of the straight body section of an inflatable member after inflation of said inflatable member.

Reference will now be made in detail to embodiments of the present invention, examples of which are illustrated in the accompanying drawings.

Figure 1A:
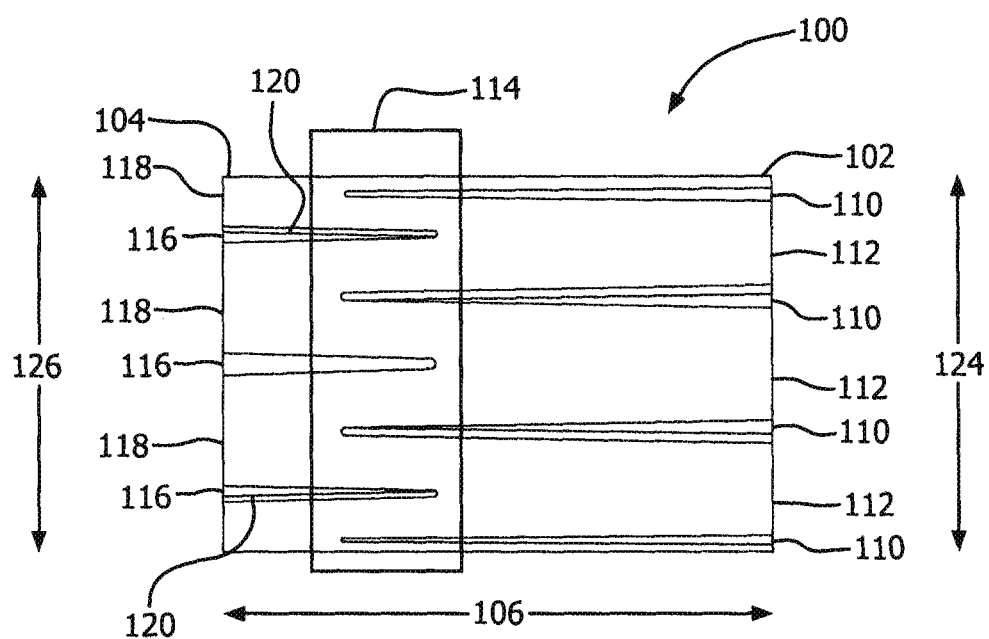
FIGS. 1A and 1B depict a "closed" ring of the invention.
Figure 1B:
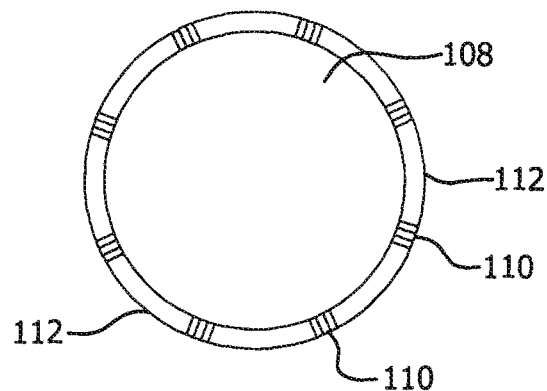
Figure 1C:
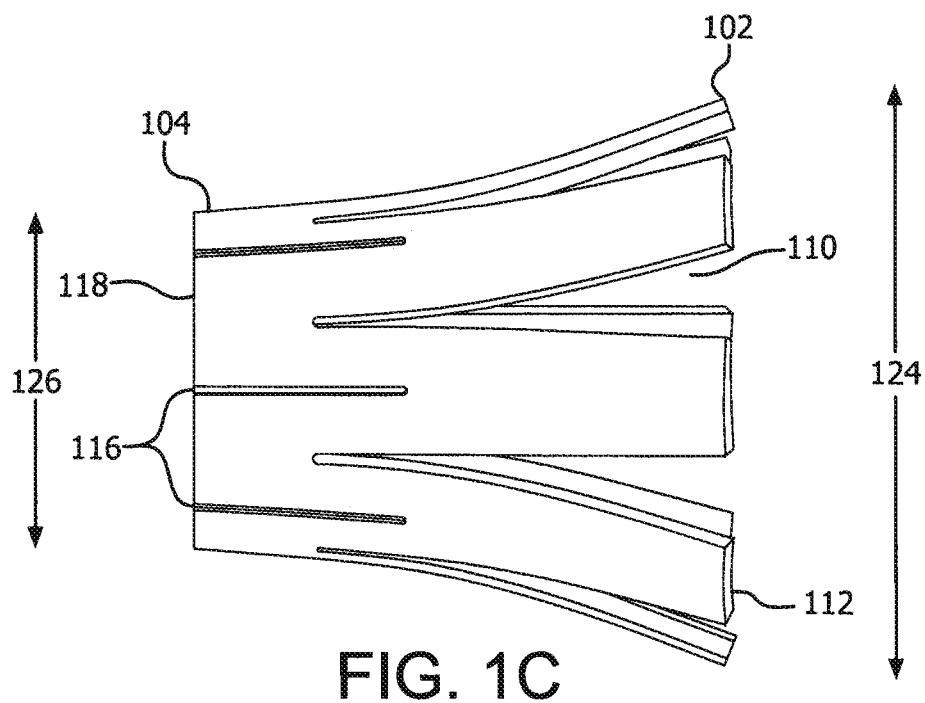
FIGS. 1C and 1D depict an "open" ring of the invention.
Figure 1D:
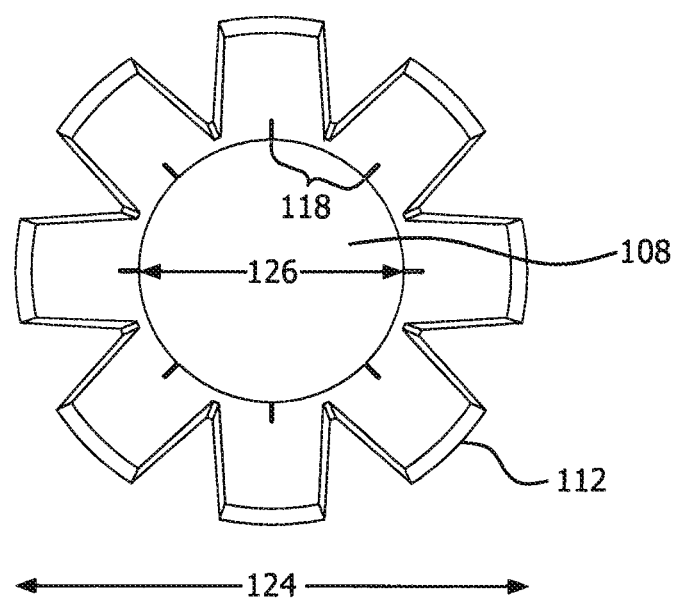

FIGS. 1A and 1B depict a "closed" ring member 100 and FIGS. 1C and 1D depict an "open" ring member 100 (i.e. wherein fingers 112 are spread open). FIG. 1A is a side view of closed ring member 100 and FIG. 1B is an end view of the closed ring member 100. FIG. 1C is a side view of open ring member 100 and FIG. 1D is an end view of the open ring member 100.

As shown in FIGS. 1A through 1D, one embodiment of the invention comprises a pivoting ring member 100 that comprises a first end 102 and second end 104. Ring member 100 also comprises a length, as depicted as arrow 106, and a lumen 108 therethrough (FIG. 1B). When ring member 100 is closed, lumen 108 has a diameter that is, more or less, constant through length 106 of ring member 100. As illustrated by arrows 124 and 126, diameter 124 of first end 102 has the same diameter 126 of second end 104. Lumen 108 allows ring member 100 to be placed over an inflatable member or any other object. Ring member 100 further comprises a plurality of slits 110 and fingers 112 near first end 102. Slits 110 are cut through the thickness of ring member 100 and are made partially down length 106 of ring member 100 (which may or may not have gaps between the slits). In between slits are fingers 112 that spread apart as first end 102 increases in diameter, as described below.

Ring member 100 also comprises slots 116 and ring members 118 near second end 104. Slots 116 are cut out of ring member 100 creating gaps 120 around the circumference of second end 104. These gaps will decrease in size as second end 104 decreases in diameter and first end 102 increases in diameter. Slots 116 allow ring members 118 to come together, thus allowing the reduction in diameter 126 of second end 104. In one embodiment, slots 116 are offset (staggered) from slits 110. In another embodiment, slots 116 and slits 110 overlap in pivot region 114. It has been discovered that offsetting the slots on either end of the band and then overlapping the slits allow the ring of the invention to have a pivoting effect. This allows the ring member 100 to pivot in region 114. Thus, as first end 102 increases in diameter 124 and second end 104 decreases in diameter 126, pivot region 114 creates a fulcrum, allowing ring member 100 to pivot. Another embodiment of the invention comprises a pivoting ring that comprises a first end and second end wherein when the first end increases in diameter the second end decreases in diameter. In another embodiment, the decrease in diameter generates an inward force.

As stated above, pivoting ring member 100 comprises a first end 102 and second end 104 wherein when first end 102 increases in diameter the second end 104 decreases in diameter. This is illustrated in FIGS. 1C and 1D. When ring member 100 is in the open configuration, fingers 112 spread apart increasing the first end 102 diameter 124 and decreasing second end diameter 126. In one embodiment, a radial force pushes fingers 112 outwardly and causes the increase in diameter of first end 102. One example of a radial force that spread fingers 112 apart is by placing ring member 100 over an inflatable member and inflating said member. In another embodiment, the radial force is from a tube that increases in diameter, forcing fingers 112 outwardly.

In another embodiment, a final (smaller) diameter 126 can be predetermined and be "locked" to a final diameter via mechanical interference. The "lock" on diameter 126 of second end 104 means that forces (e.g. balloon pressure) on first end 102 will not allow second end 104 of the band to compress together any further once it is in its predetermined diameter due to ring members 118 touching each other, thus locking diameter 126 of said second end 104. The reduction in diameter can be tailored by adjusting the width of slots 116. The desired reduction in the circumference of the band is the total amount of material removed in the cutting process. For example, if a 0.254 centimeter (0.100 inch) inner diameter is to be reduced to a 0.2032 centimeter (0.080 inch) diameter, the circumference would need to be reduced from 0.7976 centimeter (0.314 inch), (π*0.254 centimeter), to 0.6375 centimeter (0.251 inch), (π*0.2032 centimeters), or a reduction of 0.16 centimeter (0.063 inch). This could be achieved by 8 cuts of 0.02032 centimeter (0.008 inch) width around the circumference of the band (a reduction of (0.1626 centimeter (0.064 inch)). Additional geometric parameters which could be varied, include, but are not limited to, the length of the cuts, the number of the cuts, the overlap of the cuts, and the ratio of the long cuts to the short cuts. These parameters could be varied to achieve desired force and deflection characteristics. Examples of outputs which could be changed are the ratio of the applied balloon pressure to the sealing pressure, the ratio of diameter reduction to balloon volume, or the location of the virtual "pivot point" (or pivot region) of the band (114 in FIG. 1).

Said ring can be made from any resilient material with appropriate stiffness. Such materials include, but not limited to, nitinol, Titanium alloys, Iron Alloys, and Cobalt Chromium alloys or polymers such as Nylon, Polycarbonate, Polyester, Polyimide, Polyether block Amide, etc. Resilient materials allow ring member 100 to return back to its original shape, or close to its original shape, when the force(s) which increase the diameter of first end 102 is reduced.

In another embodiment, ring member 100 can be made from a plastically deformable material, such as a polymer or metal such as stainless steel. In this embodiment, when the radial force, which increases the diameter of first end 102, is reduced, ring member 100 will stay in the open position (as illustrated in FIGS. 1C and 1D). This embodiment could be useful for a permanent seal on an implantable occlusion balloon, for example.

One use of the ring of the invention is that said ring can be used to seal at least one end of an inflatable member. One embodiment of the invention is shown in FIGS. 2A through 2C as balloon catheter 201. In this embodiment, said ring of the invention (100) is used to seal at least one end of an inflatable member on the distal end of a balloon catheter. As illustrated in FIG. 2, the elongate member 203 has a proximal control end 207 and a distal functional end 209. The balloon catheter also has a proximal guidewire lumen 211 that extends through the length of the elongate member 203 and exits the distal end at a guide wire port 213. Balloon catheter 201 is shown as an "Over The Wire" configuration, as commonly known in the art. As an alternate, the catheter could have a mid-guidewire port and therefore have a "Rapid Exchange" configuration, as commonly known in the art.

The balloon catheter 201 also incorporates a proximal inflation port 215 that allows fluid communication between the inflation port 215 and the inflatable member 205. The length and inner and outer diameter of the elongate member are selected based upon the desired application of balloon catheter 201. For example, in one non-limiting embodiment, wherein balloon catheter 201 is used in percutaneous transluminal coronary angioplasty, the length of the elongate member typically ranges from about 120 cm to about 140 cm. In this embodiment, the outer diameter of the elongate member ranges from about 0.6 mm (about 0.024 inches) to about 11.5 mm (about 0.45 inches). As will be understood by the skilled artisan upon reading this disclosure, the length and/or diameter of the elongate member are in no way limiting and may be routinely modified for various applications of the medical devices of the present invention. The elongate member generally has a circular cross-sectional configuration.

Elongate member 203 must have sufficient structural integrity to permit the medical device to be advanced to distal body conduit locations without bending or buckling upon insertion and have sufficient integrity to withstand a radial force from second end 104 of pivot ring member 100 as the diameter decreases when the first end 102 of pivot ring 100 is shifting to an open configuration. Various techniques are known for manufacturing the tubular bodies. In one embodiment, the elongate member is manufactured by extrusion of a biocompatible polymer.

Figure 2D:
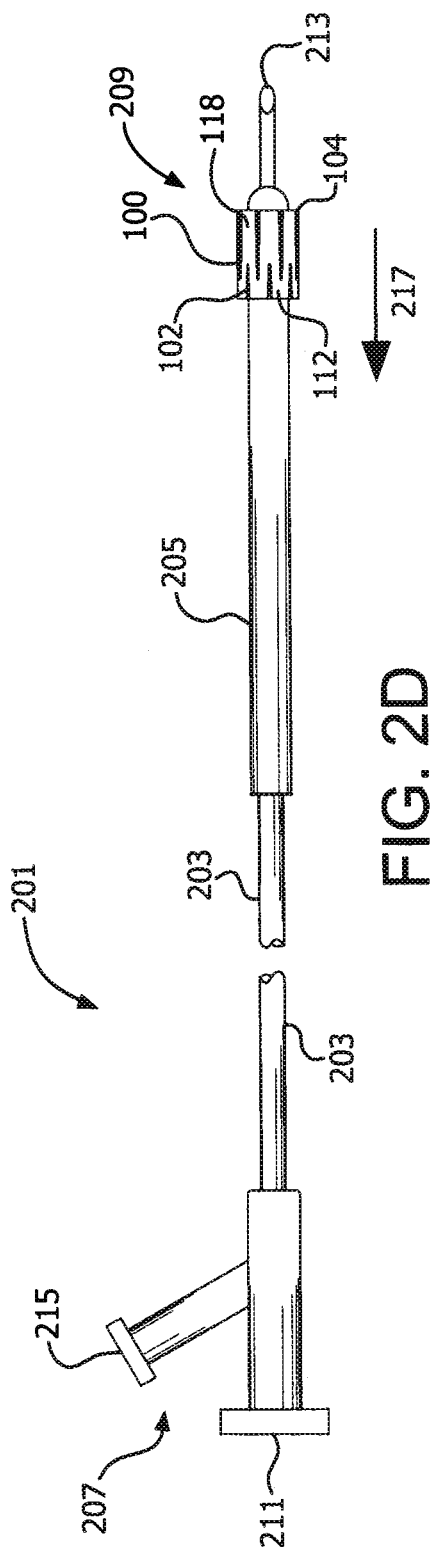
FIGS. 2D and 2E depict alternative embodiments of the invention, including having multiple rings of the invention on a balloon catheter.

As illustrated in FIGS. 2A and 2B, balloon catheter 201 comprises ring member 100. Ring member 100 can be slid over inflatable member 205. In this embodiment, ring member 100 is placed at the proximal end of inflatable member 205, with fingers 112 oriented toward the distal end of inflatable member 205 and ring members 118 oriented toward the proximal end of inflatable member 205. In another embodiment, ring member 100 can be placed near the distal end of the balloon catheter with fingers 112 oriented toward the proximal end of inflatable member and ring members 118 oriented toward the distal end, as illustrated in FIG. 2D. Said ring member 100 can be slid over the inflatable member, as illustrated by arrow 225 in FIGS. 2A, 2B and 2E and 217 in FIGS. 2D and 2E and placed anywhere along the length of inflatable member 205. FIG. 2B depicts the same balloon catheter in FIG. 2A, except that ring member 100 is moved axially toward the distal portion of inflatable member 205. Note that there is a relationship between inflation port(s) (see, 325 in FIG. 3A) and the pivot ring of the invention. A skilled artisan would understand where to position the pivot ring of the invention in relation to inflation port(s) on a catheter. In this embodiment, first end 102 should be oriented to face the inflation port. In another embodiment, the inflation port can be at either end of the balloon or anywhere along the length of the balloon.

FIG. 2C depicts inflatable member 205 in an expanded configuration. As inflatable member 205 expands, inflatable member forces first end 102 of ring member 100 to increase in diameter, as illustrated by arrows 223, and second end 104 decreases in diameter, as illustrated by arrows 221, which generates an inward force. As second end 104 decreases in diameter, it constricts against elongate member 203 and inflatable member 205 resulting in a seal of at least one end of inflatable member 205. Furthermore, said inward force also acts to embed the end of the ring member into the balloon preventing axial movement. This seal can be placed anywhere along the length of inflatable member 205, thus creating an inflatable member that can be customized in length. Thus, another embodiment of the invention comprises using the ring of the invention to adjust the working length of an inflatable member.

Figure 2E:
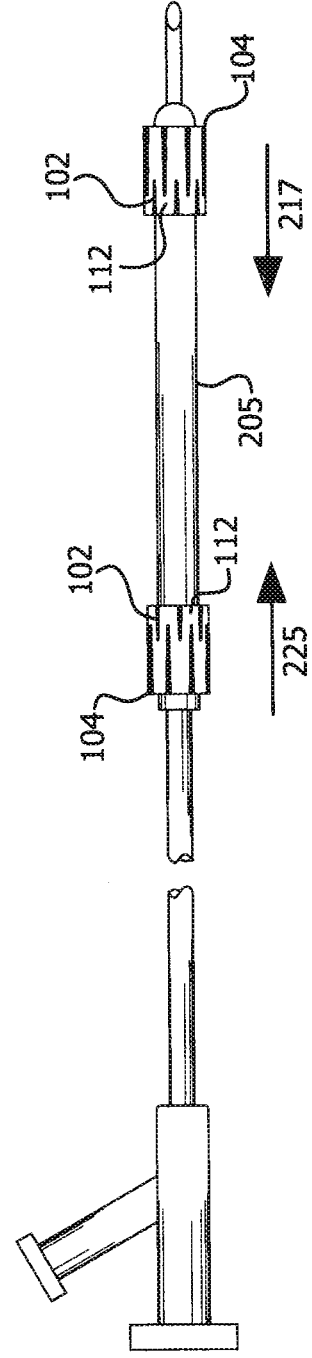

As inflatable member 205 increases in diameter, the diameter of first end 102 of ring member 100 also increases causing second end 104 to further decrease in diameter. The decrease in diameter causes sealing force between inflatable member 205 and the elongate member 203 to become stronger. Thus, as the diameter of second end 104 of ring member 100 becomes smaller, the seal between inflatable member 205 and elongate member 203 becomes tighter. Ring member 100 creates a seal that is beneficial in applications requiring higher inflation pressures. Compared to traditional seals requiring adhesives to prevent failure, this seal offers a mechanical action which acts to tighten with increasing pressure. As the inflatable member inflates, the side of the band is lifted which pivots the opposite part of the band around a fulcrum in the middle of the band. The pivoting causes the opposing part of the band to tighten around elongate member 203 allowing for a higher-pressure seal. In one embodiment, more than one ring member 100 can be placed in any orientation, moved, and placed in any area of inflatable member 205 on catheter 201. As depicted in FIG. 2E, at least 2 rings can be placed on an inflatable member. In this embodiment, there is a proximal and distal seal as inflatable member 205 expands. In another embodiment, three, four, five or more pivot rings of the invention can be placed on an inflatable member. Although the embodiment depicted in FIG. 2 depicts a balloon catheter, any medical device with an inflatable member is also contemplated as part of this invention. Again, note that there is a relationship between inflation port(s) (see, 325 in FIG. 3A) and the pivot rings of the invention. A skilled artisan understands that in the embodiment depicted in FIG. 2E, there needs to be at least one inflation port between the rings.

Since the ring of the invention can be slid to any position along the length (or along the axis) of an inflatable member (i.e. inflatable portion of inflatable member) the inflatable member can be customized in size (i.e. length) and/or working length.

As shown in FIG. 2, at least one inflatable element 205 is provided at the distal end of the elongate member. An example of an inflatable member useful in the present invention is a medical balloon. Other forms of inflatable elements include, but are not limited to balloon, expandable catheter, hoses, expandable pipes, and the like.

Thus, one embodiment of the invention comprises a medical device comprising, an inflatable member having opposing ends, a smaller deflated profile and a larger inflated profile, a working length, and a ring member having opposing ends, said ring member being slidable to any position between the opposing ends of the deflated inflatable member, wherein when one opposing end of said ring member increases in diameter, the other opposing end of said ring member decreases in diameter upon inflation of the inflatable member. In one embodiment, the increase in the diameter of the ring member in one opposing end is driven by the inflatable member. In another embodiment, the decrease in diameter of one of said opposing end of said ring member restricts inflation of a portion of said inflatable member. In another embodiment, said inflatable member is disposed over an elongate member. In another embodiment, said elongate member is a catheter or a guidewire. In another embodiment, the decrease in diameter of the opposing end of said ring member makes said end constrict against said inflatable member and/or said elongate member. In another embodiment, the constriction of the opposing end of said ring member against said inflatable member and/or said elongate member result in a seal of at least one end of said inflatable member. In another embodiment, as the diameter of the opposing end of said ring member decreases, the opposing end of said ring member further constricts against said inflatable member and/or said elongate member resulting in a tighter seal of at least one end of said inflatable member. In another embodiment, the decrease in diameter of one of the opposing end of said ring member restricts axial movement of said ring member. In another embodiment, said inflatable member is a medical balloon. In another embodiment, said medical balloon comprises expanded polytetrafluoroethylene (ePTFE). In another embodiment, the position of said ring member adjusts the working length of said medical balloon. In another embodiment, said medical balloon further comprises a balloon cover. In another embodiment, said balloon cover comprises ePTFE. In another embodiment, said medical balloon comprises a drug coating on said balloon and/or balloon cover. In another embodiment, said ring member comprises a resilient metal. In another embodiment, said resilient metal is nitinol. In another embodiment, the position of said ring member adjusts the working length of the expandable portion of said inflatable member.

In another embodiment, the invention comprises a medical device comprising an inflatable member having opposing ends, a smaller deflated profile and a larger inflated profile, a working length, and a ring member having opposing ends, wherein said ring has a position between the ends of the said inflatable member and wherein an increase in diameter on one of the opposing ends of said ring member results in a compressing force in the other opposing end of said ring member. In one embodiment, the increase in the diameter of said ring member in one opposing end is driven by said inflatable member. In another embodiment, said compressing force is caused by a decrease in diameter of one of the opposing ends of said ring member. In another embodiment, said decrease in diameter of one of said opposing ends of said ring member restricts axial movement of said ring member. In another embodiment, said decrease in diameter of one of said opposing ends of said ring member restricts inflation of a portion of said inflatable member. In another embodiment, said inflatable member is disposed over an elongate member. In another embodiment, said elongate member is a catheter or a guidewire. In another embodiment, said compressive force causes said opposing end of said ring member to constrict against said inflatable member and/or said elongate member. In another embodiment, as the diameter of said opposing end of said ring member decreases, said opposing end of said ring member further constricts against said inflatable member and/or said elongate member resulting in a tighter seal of at least one end of said inflatable member. In another embodiment, the inflatable member is a medical balloon. In another embodiment, said medical balloon comprises ePTFE. In another embodiment, the position of said ring member adjusts the working length of said medical balloon. In another embodiment, said medical balloon further comprises a balloon cover. In another embodiment, said balloon cover comprises ePTFE. In another embodiment, said medical balloon comprises a drug coating on said balloon and/or balloon cover. In another embodiment, said ring member comprises a resilient metal. In another embodiment, said resilient metal is nitinol.

Another embodiment of the invention comprises a method of adjusting the working length of an inflatable member comprising disposing at least one ring member onto an inflatable member having a length, wherein said ring member has opposing ends and when one opposing end of said ring member increases in diameter, the other opposing end of said ring member decreases in diameter upon inflation of the inflatable member, and sliding the at least one ring member to a predetermined position along the length of said inflation member. In one embodiment, increasing the diameter of one of the opposing ends of said at least one ring member results in a compressing force in the other opposing end of said ring member. In another embodiment, the increase in the diameter of said one opposing end of said at least one ring member is driven by said inflatable member. In another embodiment, there are at least two ring members disposed on said inflatable member. In another embodiment, the decrease in diameter of said one opposing end of said ring member restricts inflation of a portion of said inflatable member. In another embodiment, said inflatable member is disposed over an elongate member. In another embodiment, said elongate member is a catheter or a guidewire. In another embodiment, the decrease in diameter of the opposing end of said ring member makes said end constrict against the inflatable member and the elongate member. In another embodiment, the constriction of the opposing end of said ring member against said inflatable member and/or said elongate member results in a seal of at least one end of said inflatable member. In another embodiment, as the diameter of the opposing end of said ring member decreases, said opposing end of said ring member further constricts against said inflatable member and/or said elongate member resulting in a tighter seal of at least one end of said inflatable member. In another embodiment, the decrease in diameter of one of said opposing end of said ring member restricts axial movement of said ring member. In another embodiment, said inflatable member is a medical balloon. In another embodiment, said medical balloon comprises ePTFE. In another embodiment, said medical balloon further comprises a balloon cover. In another embodiment, said balloon cover comprises ePTFE. In another embodiment, said medical balloon comprises a drug coating on said balloon and/or balloon cover. In another embodiment, said ring member comprises a resilient metal. In another embodiment, said resilient metal is nitinol.

In one embodiment, said inflatable member is a medical balloon. In another embodiment, said medical balloon has a concentric inflation modality. The medical balloon according to the present invention may be made using any materials known to those of skill in the art. Commonly employed materials include the thermoplastic elastomeric and non-elastomeric polymers and the thermosets including the moisture and/or heat curable polymers. Examples of suitable materials include but are not limited to, polyolefins, polyesters, polyurethanes, polyamides, polyether block amides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See, U.S. Pat. No. 5,500,181, for example. As used herein, the term copolymer shall be used to refer to any polymeric material formed from more than one monomer.

In an alternative embodiment, as used herein, the term "copolymer" shall be used to refer to any polymer formed from two or more monomers, e.g. 2, 3, 4, 5 or more. Useful polyamides include, but are not limited to, nylon 12, nylon 11, nylon 9, nylon 6/9 and nylon 6/6. The use of such materials is described in U.S. Pat. No. 4,906,244, for example.

Non-limiting examples of some copolymers of such materials include the polyether-block-amides, available from Elf Atochem North America in Philadelphia, Pa. under the tradename of PEBAX®. Another suitable copolymer is a polyetheresteramide.

Suitable polyester copolymers, include, for example, polyethyelene terephthalate (PET) and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and the like may also be employed herein. Other styrenic block copolymers include acrylonitrile-styrene and acrylonitrile-butadiene-styrene block copolymers. In an alternative embodiment, it is possible to use in the present invention block copolymers wherein the particular block copolymer thermoplastic elastomers in which the block copolymer is made up of hard segments of a polyester or polyamide and soft segments of polyether.

Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials which can be employed in balloon formation are further described in, for example, U.S. Pat. No.s 6,406,457; 6,284,333; 6,171,278; 6,146,356; 5,951,941; 5,830,182; 5,556,383; 5,447,497; 5,403,340; 5,348,538; and 5,330,428.

The above materials are intended for illustrative purposes only, and not as limitations on the scope of the present invention. Suitable polymeric materials available for use are vast and too numerous to be listed herein and are known to those of ordinary skill in the art.

Balloon formation may be carried out in any conventional manner using known extrusion, injection molding and other molding techniques. Typically, there are three major steps in the process which include extruding a tubular preform, molding the balloon and annealing, or heating and cooling as appropriate for the particular material set(s), the balloon. Depending on the balloon material employed, the preform may be axially stretched before it is blown. Techniques for balloon formation are described in U.S. Pat. No. 4,490,421, RE32,983, RE33,561 and U.S. Pat. No. 5,348,538.

The inflatable member may be attached to an elongate member by various bonding means known to the skilled artisan. Examples include, but are not limited to, solvent bonding, thermal bonding, adhesive bonding, and heat shrinking or sealing. The selection of the bonding technique is dependent upon the materials from which the inflatable element and elongate member are prepared. Refer to U.S. Pat. No. 7,048,713, which is incorporated by reference herein in its entirety, for general teachings relating to the bonding of a balloon to a catheter.

In another embodiment, the balloon comprises expanded polytetrafluoroethylene (ePTFE), as essentially taught in U.S. Pat. No. 6,120,477 (Campbell, et al.), which is incorporated herein by reference for all purposes. In another embodiment, the balloon, which can be made from any material described above or known in the art, is covered with a balloon cover, as essentially taught in U.S. Pat. No. 6,120,477 (Campbell, et al.). In one embodiment said balloon cover comprise ePTFE. One important feature in selecting a material to make a balloon and/or a balloon cover is to allow the end of the ring member that is decreasing in diameter to embed into the material in order to get a tighter grip and/or a better seal. In one embodiment, said medical device comprises a polyurethane balloon comprising an ePTFE balloon cover and the ring member of the invention. In one alternative embodiment, said medical device comprises a PET balloon comprising an ePTFE balloon cover and the ring member of the invention.

In another embodiment, the ring of the invention can be used to make a size adjustable single lumen high-pressure balloon catheter that shares a guidewire lumen and an inflation lumen. This is significant because a single lumen catheter has a smaller diameter (or French size), which is desirable. The ring of the invention enables a size adjustable high-pressure balloon (about 10 atm to about 30 atm, depending on diameter and length) to be mounted on a singe lumen catheter and to inflate said balloon to high pressures.

Figure 3A:
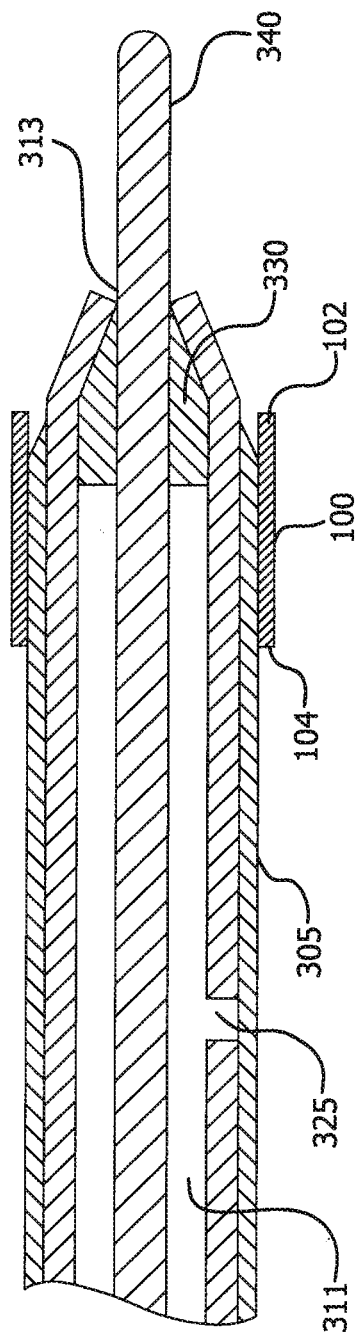
FIGS. 3A and 3B depict a cross-section of a high-pressure balloon mounted on a single lumen catheter before (3A) and after (3B) inflation of said balloon.
Figure 3B:
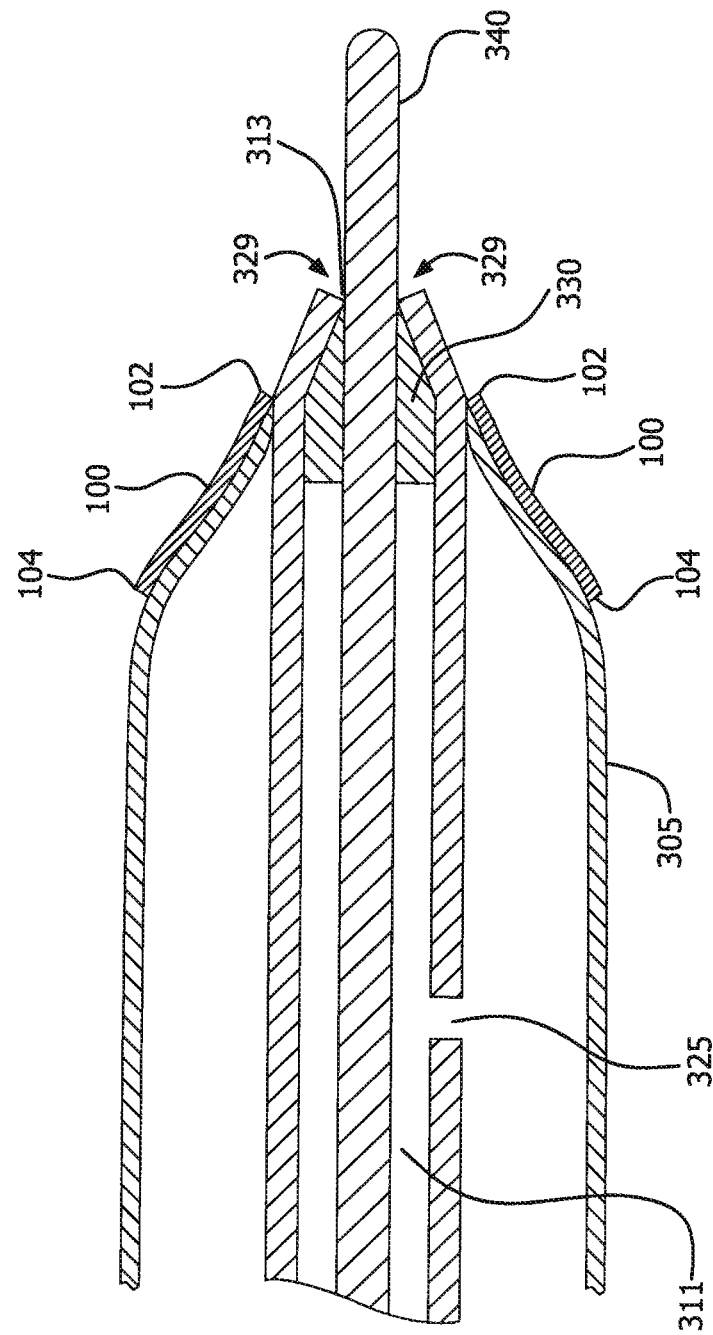

As depicted in FIGS. 3A and 3B, a single lumen high-pressure balloon catheter can comprise a high-pressure balloon 305, lumen 311, at least one inflation port 325, and pivot ring member 100 located near the distal end of the outer wall of the catheter and/or on a portion of the high-pressure balloon. In another embodiment, said single lumen high-pressure balloon catheter also comprises a sealing agent 330 located toward the distal end of the inner wall of the catheter. Said high-pressure balloon can be mounted on the catheter by methods described above and/or known in the art.

When a guidewire 340 (or other tubular device such, as a catheter) is advanced into lumen 311 and to, or past, distal port 313 it occludes distal port 313. When inflation media is added from the proximal end (e.g. see, 215 in FIG. 2) there will be no, or minimal, leaking of the inflation media from distal port 313 thus allowing the balloon to inflate through the inflation port(s) 325. As more inflation media is added, the media will flow through the inflation port(s) 325 and into balloon 305 thereby increasing the pressure within the system and causing balloon 305 to inflate. As balloon 305 inflates, as depicted in FIG. 3B, ring member 100 will begin to increase in diameter at first end 102 and decrease in diameter at the second end 104 (as described above). As second end 104 decreases in diameter, it generates an inward force, depicted by arrows 329, which compresses distal port 313 (or a specific area of the catheter) and optional sealing agent 330 around guidewire 340 (or other tubular structure). As the pressure inside the balloon increases, thus decreasing the diameter of second end 104, the stronger the compressive force becomes at distal end 313 and the tighter the seal between the guidewire 340, distal end 313, and optional sealing agent 330. In this embodiment, there will be no, or minimal, inflation media leakage as the balloon is inflating to its final pressure. Without ring member 100, distal port 313 will begin to leak at a lower pressure, making it unsuitable for applications such as balloon angioplasty. This system allows for having a high-pressure balloon using a single lumen catheter. In one embodiment, said high-pressure balloon comprises a balloon with about an 8 mm expanded diameter that can be inflated to a pressure up to about 14 atm. In another embodiment, said sealing agent is selected from the group consisting of silicone, urethane, fluoroplastics, or polyether block amide. In another embodiment, said other tubular structure is a catheter, guidewire or hypotube. In another embodiment, said single lumen high-pressure balloon catheter comprises at least two pivoting ring members of the invention, as depicted in FIG. 2E.

In another embodiment, there is a small gap between the distal port 313 and guidewire 340 (or other tubular structure). The small gap allows guide wire 340 (or other tubular structure) to slide smoothly through distal end of the catheter, including distal port 313. As inflation media is added into lumen 311, a small of amount of leaking can occur, however as balloon 305 inflates, ring member 100 will increase in diameter at first end 102 and decrease in diameter at the second end 104 (as described above). As second end 104 decreases in diameter, it generates an inward force, depicted by arrows 329, which compresses the distal end of the catheter, including distal port 313 around guidewire 340 (or other tubular structure). As the pressure inside the balloon increases, thus decreasing the diameter of second end 104, the stronger the compressive force becomes at distal end of the catheter and the tighter the seal between the guidewire 340 and distal end of the catheter, including distal port 313. In another embodiment, the catheter comprises sealing agent 330 located toward the distal end of the inner wall of the catheter.

Medical devices of the present invention are useful in treating sites in a body conduit or delivering interventional devices as described above. In one embodiment, the medical device of the present invention is used in angioplasty procedures. In this method, the medical device of the present invention is placed percutaneously and advanced so that the inflatable member, in a smaller diameter profile, is adjacent to a vascular treatment site. In one embodiment, said one or more rings of the invention can be adjusted prior to insertion in the body and/or in situ when said inflatable member is adjacent to vascular treatment site. Generally, the treatment site is a stenosis caused, for example, by plaque or a thrombus. The inflatable member of the medical device is then inflated at a pressure or force sufficient to inflate the inflatable member. After the stenosis is compressed to or beyond the native diameter of the lumen, the inflatable element is evacuated and the medical device is withdrawn from the body lumen. In another embodiment, said medical devices of the present invention are useful for delivering an interventional device to a treatment site. In another embodiment, the working length of the inflatable member is customized to the length of the stenosis to be treated and/or to the length of an interventional device. As used herein, "body conduit" comprises an artery, vein and/or other lumen.

Another embodiment of the invention comprises a method of treating a site in a body conduit with a medical device as described herein, said method comprising the steps of determining the appropriate length of the inflatable member required, moving the ring of the invention along the length of the inflatable member to the appropriate location of the inflatable member, positioning within a body conduit the medical device of the invention so that the inflatable element is in a non-inflated (such as in a folded or comparable configuration) form is adjacent to a treatment site; and inflating the inflatable element at a pressure or force sufficient to inflate the inflatable element. The steps of determining the appropriate length of the inflatable member and moving the ring of the invention along the length of the inflatable member to the appropriate location may be carried out either prior to positioning the medical device in the body conduit or in situ once the medical device is placed in the body conduit, or some combination thereof. In one embodiment, said inflatable element expands an interventional device. In another embodiment, said interventional device is a stent. In another embodiment, said interventional device is a stent-graft. In another embodiment, said stent comprises nitinol and/or stainless steel, as commonly known in the art. In another embodiment, said treatment site is an artery, vein and/or other lumen within a body.

Another embodiment of the invention comprises creating a customizable stent length and customizing the length of the delivery balloon. For example, as disclosed in U.S. Patent Application Publication U.S. 2009/0182413 (which is incorporated by reference herein for all purposes), the stent with polymer interconnecting webs can be cut to a preferred size by medical staff prior to insertion in the body. By providing at least one ring of the invention in combination with any size balloon, the working length of the balloon can be adjusted to the length of the stent. In another embodiment, said customizable stent comprises stent rings interconnected by a graft, tube, film, polymer links and/or any material known in the art, such as ePTFE.

Thus, another embodiment of the invention comprises a medical stenting system comprising a medical balloon having opposing ends, a smaller deflated profile and a larger inflated profile, and a working length, at least one ring member having opposing ends, wherein an increase in diameter of one of the opposing ends of said ring member results in a compressing force in the other opposing end of said ring member, wherein said ring member has a position between the opposing ends of said inflatable member, and a customizable stent that can be adjusted to a predetermined length. In one embodiment, the position of said ring adjusts the working length of said medical balloon. In another embodiment, said stent is disposed over the working length of said medical balloon. In another embodiment, said medical balloon is disposed over an elongate member. In another embodiment, said elongate member is a catheter. In another embodiment, said customizable stent comprises stent rings interconnected by polymer webs. In another embodiment, said customizable stent is customized by cutting said polymer webs and removing stent rings. In another embodiment, said medical balloon comprises ePTFE. In another embodiment, said medical balloon further comprises a balloon cover. In another embodiment, said medical balloon cover comprises ePTFE. In another embodiment, said medical balloon comprises a drug coating on said balloon and/or balloon cover. In another embodiment, said ring member comprises a resilient metal. In another embodiment, said resilient metal is nitinol.

In another embodiment, the invention also comprises a method of introducing a customizable stent into a body conduit comprising, providing a customizable stent and a medical balloon having opposing ends, a smaller deflated profile and a larger inflated profile, and a working length, adjusting said customizable stent to a predetermined length, adjusting said working length of said medical balloon by disposing and sliding at least one ring member between said opposing ends of said medical balloon, wherein said ring member comprises opposing ends and an increase in diameter on one of the opposing ends of said ring member results in a compressing force in the other opposing end of said ring member, disposing said stent onto the working length of the medical balloon, and inserting said medical balloon, at least one ring member and stent into a body conduit. In one embodiment, said medical balloon and said stent is delivered to a predetermined site within said body conduit and said working length of said medical balloon is expanded thereby delivering said stent disposed on said balloon. In another embodiment, said customizable stent comprises stent rings interconnected by polymer webs. In another embodiment, said customizable stent is customized by cutting said polymer webs interconnecting said stent rings and removing said stent rings. In another embodiment, said method comprises at least two ring members and sliding said ring members adjusts the working length of said medical balloon. In another embodiment, said medical balloon is disposed over an elongate member. In another embodiment, said elongate member is a catheter. In another embodiment, said medical balloon comprises ePTFE. In another embodiment, said medical balloon further comprises a balloon cover. In another embodiment, said balloon cover comprises ePTFE. In another embodiment, said medical balloon comprises a drug coating on said balloon and/or balloon cover. In another embodiment, said ring member comprises a resilient metal. In another embodiment, resilient metal is nitinol.

Another embodiment of the invention comprises placing the at least one ring of the invention over a balloon used to deliver drugs. Drug eluting balloons may comprise a coating of a drug on the balloon and/or on another surface adjacent to the balloon which is designed to elute only when the balloon is expanded. In another embodiment, said drug eluting balloon can weep and/or deliver a drug though the surface of the balloon and/or balloon cover. The use of at least one ring of the invention can determine the area of the drug eluting balloon that can be expanded and thus determine the amount of drug and/or pinpoint the area and/or control the dose of drug delivered to a body conduit. Thus, drug elution can be controlled by adjusting the working length of the balloon by moving the ring(s) of the invention to the desired location of a drug eluting balloon. In one embodiment, said drug eluting balloon has multiple drugs along the length of said balloon which can be delivered by moving said pivot ring(s) of the invention along the length of the drug eluting balloon. In addition, said expansion of the balloon can be controlled by moving multiple rings to specific areas of the balloon in coordination with inflation ports. In another embodiment, said drug is placed on only a portion of a balloon, for example on the proximal end. In this embodiment, the ring(s) can be moved to only inflate the portion of the balloon without drug, thereby expanding a body conduit. Then the pivot ring(s) of the invention can be moved, in situ, toward the distal end to expand the portion of the balloon with a drug, to deliver the drug to the expanded body conduit. This system allows for body conduit expansion, without drug delivery, and then delivering a drug to the expanded body conduit without having to remove the balloon and inserting another. In another embodiment, said drug is selected from the group consisting of paclitaxel, dexamethasone, rapamycin, any analogues thereof, and any combination thereof.

In another embodiment, the pivot ring of the invention can be used to deliver multiple drug treatments per balloon catheter. In one embodiment, for example, a balloon catheter with a 100 mm drug treatment section can be delivered to the desired treatment site where the pivot ring of the invention is positioned to only allow expansion at the distal 40 mm of said balloon. The pivot ring of the invention (or multiple pivot rings) can then be repositioned either in situ, or upon removal and manually repositioning of the said pivot ring(s), for a subsequent inflation of a previously un-expanded balloon section to deliver another drug or same drug associated with that previously un-expanded section of the balloon. This embodiment would allow for multiple drug deliveries per balloon catheter, each with a customizable treatment length.

Several embodiments of the instant invention allows for repositioning of said pivot ring(s) in situ. In one embodiment, the pivot ring of the present invention can be fixedly attached to a control means which extends to the proximal portion of the catheter allowing the clinician to adjust the position of the band along the inflatable member while the inflatable member remains in the body. In another embodiment, the control means can be a thin wall tube sized appropriately to fit over the outer diameter (OD) of the pivot ring of the invention and allowing it to be attached at a point in the band which includes the fulcrum of the pivot in the band. In this embodiment, the control tubing could extend the full length of the catheter proximally, to a point in a control handle where medical staff could pull on the tubing to reposition the band. In another embodiment, the thin wall tube could be a PTFE tube comprising a thermoplastic FEP. This tube could be heated when positioned over the band to allow the FEP to reflow and bond to the band. In another embodiment, a fiber is fixedly attached to a feature on the band. The catheter, which holds the expandable member, could include a lumen for the fiber which extends to the proximal end of the catheter. The fiber could exit the lumen at a point either distal or proximal to the band, allowing the band to be repositioned in either direction axially along the inflatable member to either lengthen or shorten the working length of the inflatable member in situ. In another embodiment, multiple means for repositioning the band can be employed on a single band to allow the band to be repositioned more distally or more proximally, multiple times throughout a procedure. In another embodiment, the control tube could have enough column and tensile strength to allow the band to repositioned in either direction along the axial length of the inflatable member. Thus, one embodiment of the invention comprises, adjusting said working length of a balloon in situ, while the balloon is in a patient by, for example, attaching a wire, tube and/or fiber to the pivot ring(s) and running said wire, tube and/or fiber to the proximal end of the catheter for medical staff to manipulate. In another embodiment, medical staff determines the working length of the balloon by moving the ring to the desired location along the length of the balloon to determine the working length of the balloon before placing the balloon into the body conduit of a patient.

Another embodiment of the invention comprises controlling the diameter of the balloon by pulling stored length out of the working length of the balloon under the ring members 118 such that when said opposing second end 104 of said ring member decreases in diameter upon inflation of the inflatable member, the stored length will be outside second end 104 (opposite first end 102) and not allowed to slip under the ring, thus controlling the diameter of the balloon. This would be useful in embodiments that involve inflatable members which incorporate a material set that foreshortens during inflation, thus requiring the storage of excess length to allow inflation to a preset diameter. These materials may comprise films, braids, knits, etc., and may comprise expanded PTFE or other suitable material compositions. Thus, in one embodiment, the ring of the invention can determine the working length and diameter of a balloon.

Another embodiment of the invention comprises a device and method whereby the ring of the invention can re-compact, or refold, a balloon after inflation. One of the problems with a non-compliant balloon is that when the balloon is inflated and deflated, the balloon does not go back to its original folded shape and creates flaps and/or wings that result in a larger balloon profile which cannot be easily removed from the patient and/or retracted into a sheath. In other words, the balloon is difficult to remove, because the material does not compact easily. Thus, one embodiment of the invention comprises configuring the fingers of the ring of the invention to be long enough to extend at least partially up to the cone of the balloon so that after deflation of the balloon, the ring pivots back to its original shape and the fingers (112, FIG. 4) help in the refolding or recompaction of the balloon. As depicted in FIG. 4A, when balloon 405 is inflated, rings 100 at first end 102 expands and second end 104 reduces in diameter. Fingers 112 spread as first end 102 expands. When the balloon is deflated, the first end 102 will begin to reduce in diameter and fingers 112 will start to come together and create folding creases 422 in balloon 405. These folding creases will help balloon 405 fold. As shown in FIG. 4B, the balloon is re-compacted due to the folding creases 422 created by fingers 112. FIG. 4C is an end view of balloon 405 and ring member 100 as it is being deflated. As shown, finger 112 creates folding creases to help the balloon fold into a more compacted state. Thus, it allows for tighter compaction of the balloon. In one embodiment, the fingers are aligned with the folds of the balloon so that when the balloon deflates, the fingers allow for refolding. In another embodiment, the balloon only includes one pivot ring that is placed toward the proximal end of a balloon, the end which will first enter a sheath upon withdrawal.

In another embodiment of the invention, a method comprises controlling the flow of a vascular graft in situ. One embodiment of the invention comprises placing the ring of the invention on a vascular graft, for example on GORE-TEX Vascular Graft (item no. V03050L, W. L. Gore and Associates, Inc., Flagstaff Ariz.), and implanting said graft in a patient. The ring may be configured to change shape due to a variety of conditions which may be imposed on the patient, the device or some combination of the two. In one embodiment, the ring of the invention made so that it is sensitive to temperature such that at body temperature, the ring of the invention is in the open position (see, FIGS. 1C and 1D) and when it is at a lower temperature the ring is in the closed position (see, FIGS. 1A and 1B). The open and closed positions of the ring of the invention can be accomplished by shape setting the ring of the invention at different temperatures by using memory alloys, like nitinol, as commonly known in the art. Thus, when the graft comprising the ring of the invention is placed in a patient, e.g. as an arteriovenous (AV) fistula, the ring is in the open position, not allowing blood flow, or reducing the amount of blood flow. During a dialysis procedure, the temperature of the ring can be lowered, e.g. by placing a bag of ice on the patient's arm to cool the ring on the AV graft, thus allowing the ring to adjust to an closed position and allowing increased blood flow. Thus, when the vascular graft is not in use for a dialyses procedure, the blood flow is reduced and would prevent or diminish outflow stenosis, which is a common occurrence with an AV graft.

Although the invention described supra mainly discussed the use of the ring of the invention for medical applications, this ring can be used for non-medical application. For example, the ring of the invention can be used to control the flow of a liquid in tube, e.g. a garden hose or other tube. When the tube dilates, the flow can be restricted and/or closed altogether. For example, a hose connection that allow for easy slip fit connection, but that tightens/seals when water is turned on and removable when water is turned off.

While particular embodiments of the present invention have been illustrated and described herein, the present invention should not be limited to such illustrations and descriptions. It should be apparent that changes and modifications may be incorporated and embodied as part of the present invention within the scope of the following claims. The following examples are further offered to illustrate the present invention.

EXAMPLES

Example 1

Constructing Pivot Ring

Figure 5A:
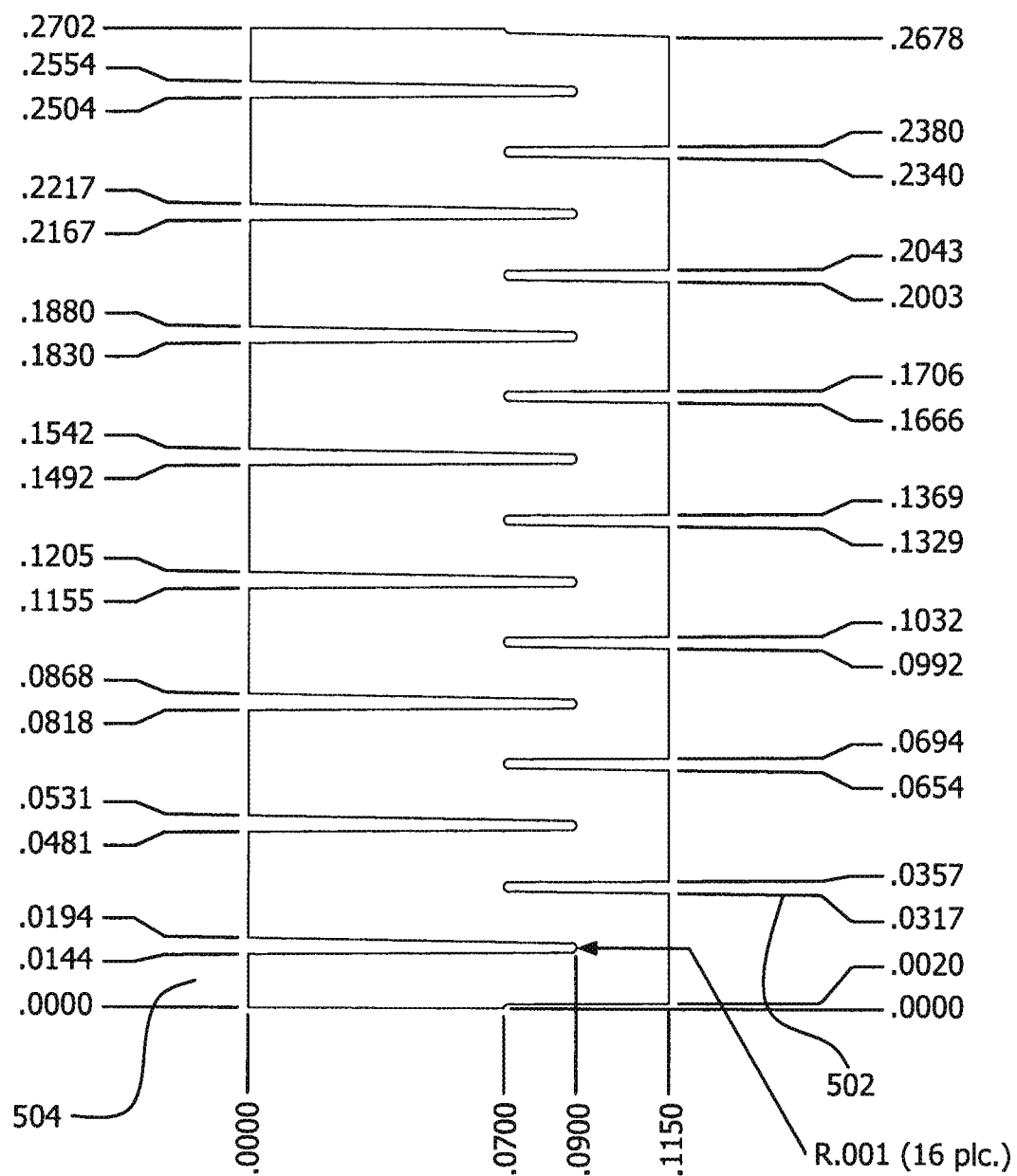
FIGS. 5A and 5B depict a flattened cut pattern of a pivot ring of the invention (5A) and said ring as cut (5B).
Figure 5B:
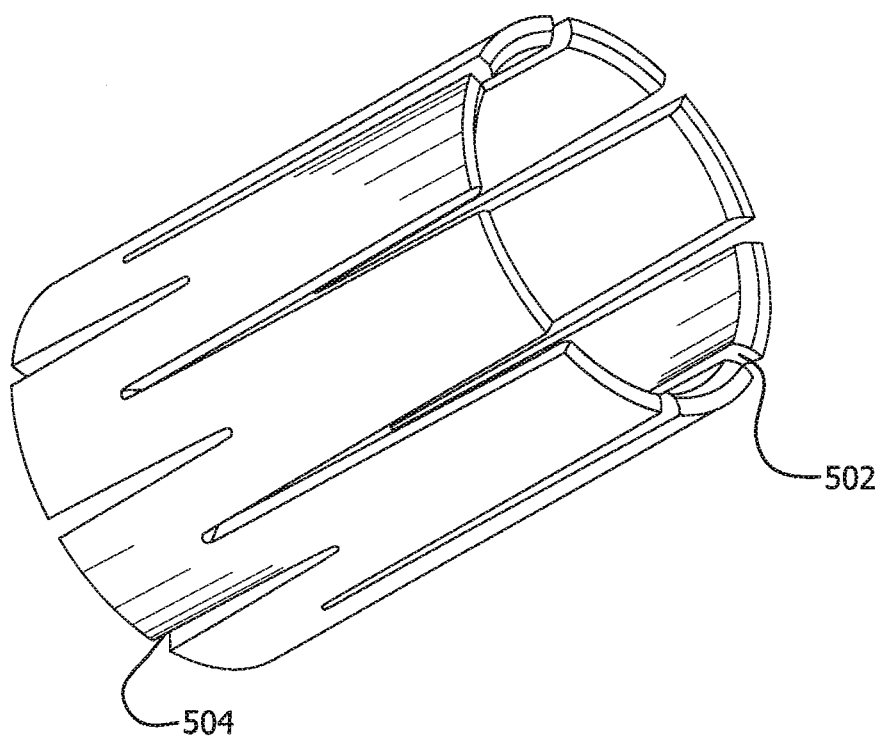

A pivot ring was made by cutting the pattern illustrated in FIG. 5 into a nitinol tube with an outside diameter of 0.086" and inside diameter of 0.074". For ease of illustration, FIG. 5 depicts the flat pattern that was cut into the tube. The cut pattern provided for 8 slots in clamping side 504 of the ring with widths of 0.004" each. Fully closed, this would result in roughly a 0.064" diameter or a 0.010" reduction in inside diameter. The cut utilized a staggered orientation of opening slits 502 and clamping slots with roughly a 2:1 length ratio (opening finger length:closing finger length). FIG. 5B is shown as tubular depiction of the resulting band.

Example 2

Constructing a Balloon Catheter

EPTFE balloon construct was made according to the teachings of U.S. Pat. No. 6,923,827, Campbell, et al. Forty layers of ePTFE were wrapped around a 6 mm mandrel at a high angle and in opposing directions. This tube was heated at 380° C. for approximately 8 minutes to fuse the layers together. The tube was removed from the mandrel and stretched which resulted in a reduction in inside diameter to at least below 0.075". The tubing was then slid onto a 0.075" stainless steel mandrel. A sacrificial overwrap of ePTFE film was placed over the tubing and its length was evenly reduced to 60% of its original length. The tube was heated at 380° C. for one minute and the sacrificial ePTFE was removed. This ePTFE tube was dipped into a 12% solution of Biospan polyurethane (DSM, Netherlands) in DMAC (N,N Dimethylacetamide). Three dips were made into the solution with a heat/drying step between each step to dry off the solvent. This tube was removed from the mandrel and inverted such that the polyurethane was on the inside diameter and the length was trimmed to approximately 60 mm (ePTFE balloon construct). A 0.063" outer diameter Nylon tube with an inner diameter of approximately 0.053" was prepared to allow for inflation. The distal end of the tube was occluded to prevent passage of inflation media. Inflation ports were skived into the side of the tube at the distal end to allow for easy passage of inflation media. A single luer fitting was fixedly attached to the proximal end of the tube with UV curing Dymax 208CTH.

The previously created ePTFE balloon construct was then placed over the distal end of the Nylon tube. The balloon construct was positioned such that the inflation ports were located just distal of the proximal edge of the balloon. ePTFE film with applied Loctite 4981 was wrapped around the proximal edge of the ePTFE balloon construct to seal the balloon to the nylon tube and prevent the passage of inflation media. The ring of Example 1 was then placed onto the balloon construct from the unsealed distal end in an orientation with clamping side 504 of the ring facing distally and opening side 502 of the ring facing proximally, towards the inflation ports (see, FIGS. 6 and 7). Expanded PTFE film with applied Loctite 4981 was wrapped around the distal edge of the balloon construct to seal the balloon to the nylon shaft and prevent the passage of inflation media.

Example 3

Illustration of Pivot Ring on a Balloon Catheter

Figure 6A:
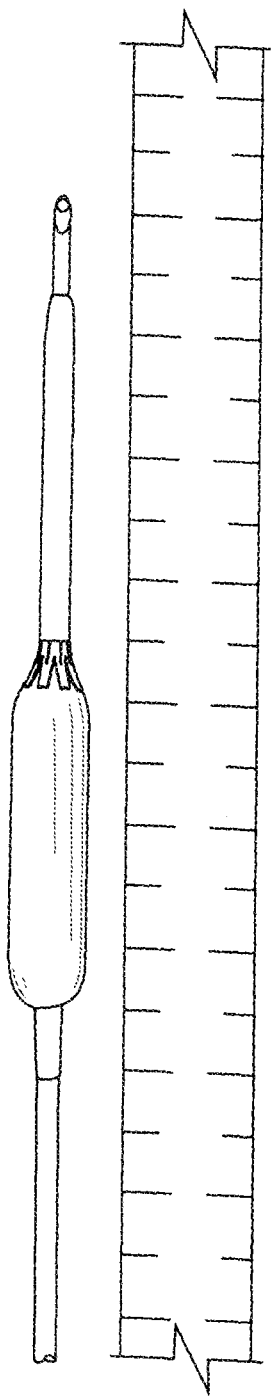
FIGS. 6A through 6D depict a balloon catheter and a pivot ring of the invention between two fixed seals. The position of the pivot ring of the invention is shown controlling the final working length of the inflated balloon.
Figure 6B:
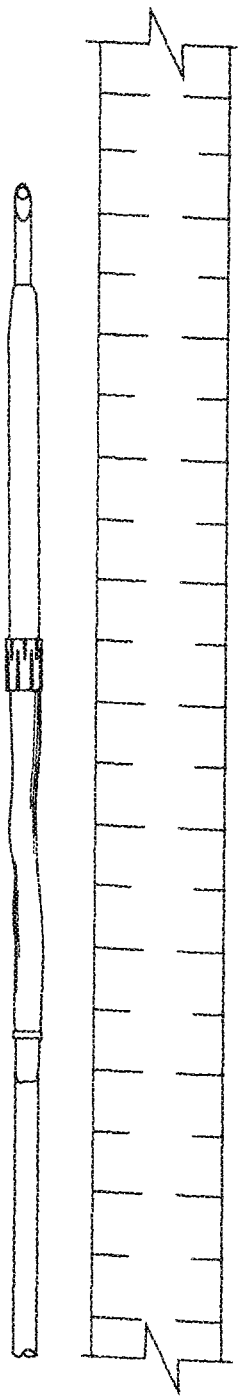
Figure 6C:
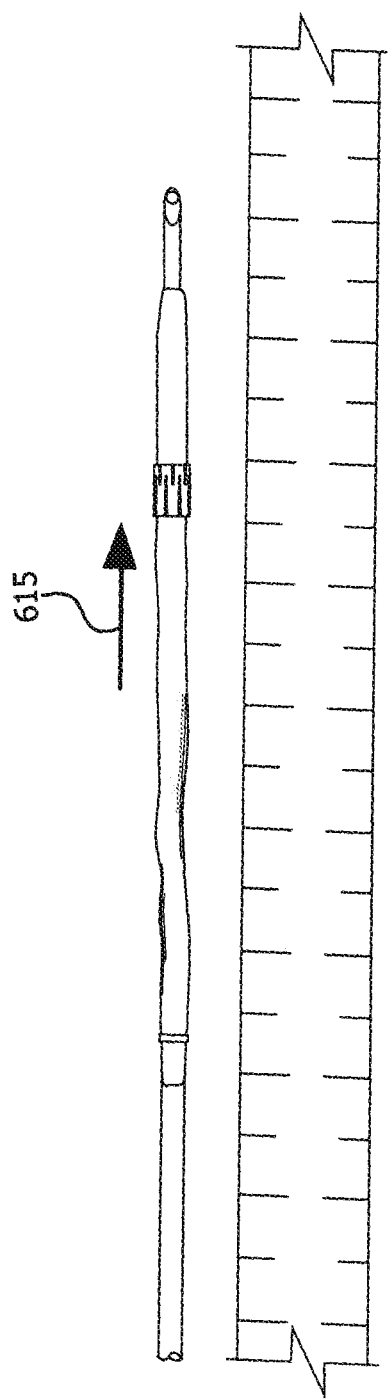
Figure 6D:
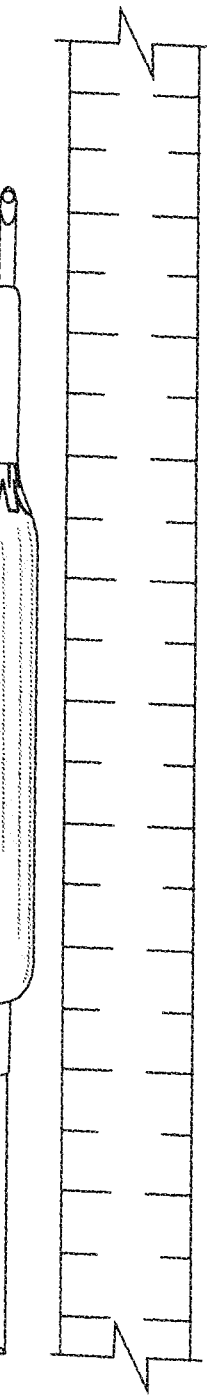
Figure 7:
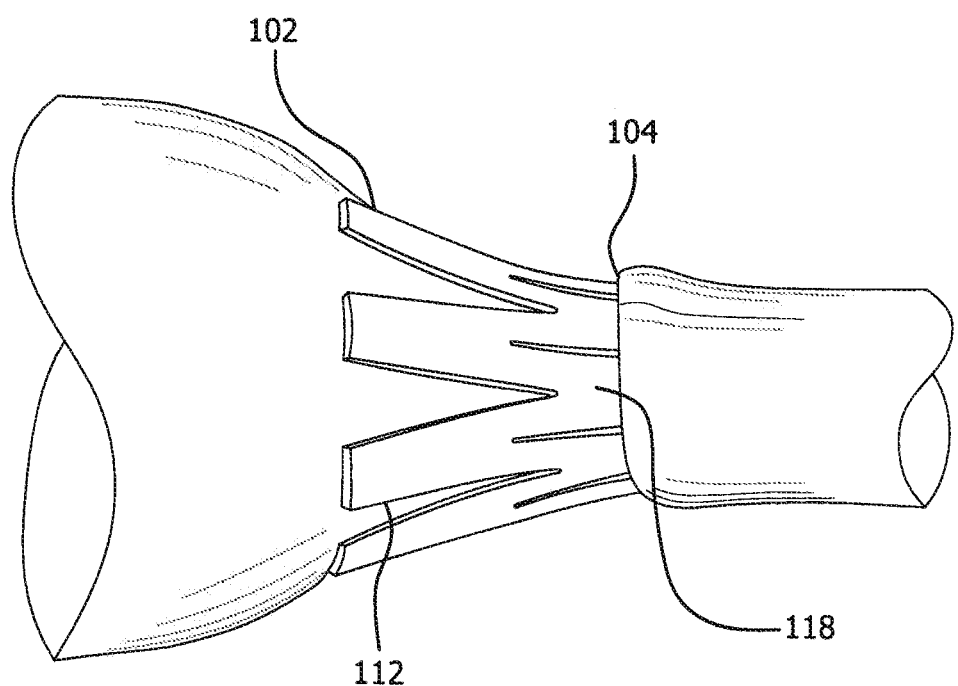
FIG. 7 demonstrates how the clamped pivot ring of the invention creates a seal and resists axial migration during inflation of a balloon.

The catheter construct of Example 2 was inflated to 6 atm's with the band in a location approximately 28 mm from the proximal seal (FIG. 6A). This resulted in a total inflated length of roughly 28 mm and no inflation media was observed passing underneath the pivoting ring member. The balloon was deflated (FIG. 6B) and the ring was repositioned distally about 10 mm (as depicted by arrow 615 in FIG. 6C). The balloon was reinflated to 8 atm's and the new inflated length of the balloon was about 38 mm (FIG. 6D) and again, no inflation media was observed passing underneath the pivoting ring. A closer image of the pivot band in its pivoted state (FIG. 7, with reference numbers as described in FIG. 1) is shown to demonstrate the band embedding into the balloon construct to make a seal and prevent axial migration upon inflation.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

What is claimed is:

1. A medical device comprising:
   an inflatable member having opposing ends, a smaller deflated profile and a larger inflated profile, and a working length; and
   a ring member having opposing ends, said ring member being slidable to a range of positions between the opposing ends of the deflated inflatable member, wherein when one opposing end of said ring member increases in diameter, the other opposing end of said ring member decreases in diameter upon inflation of the inflatable member;
   wherein the decrease in diameter of said one opposing end of said ring member restricts inflation of a portion of said inflatable member.

2. The medical device of claim 1, wherein the increase in the diameter of the ring member in one opposing end is driven by the inflatable member.

3. The medical device of claim 1, wherein said inflatable member is disposed over an elongate member.

4. The medical device of claim 3, wherein said elongate member is a catheter or a guidewire.

5. The medical device of claim 3, wherein the decrease in diameter of the opposing end of said ring member makes said opposing end constrict against said elongate member.

6. The medical device of claim 5, wherein the constriction of the opposing end of said ring member against said elongate member result in a seal of at least one end of said inflatable member.

7. The medical device of claim 6, wherein as the diameter of the opposing end of said ring member decreases, the opposing end of said ring member further constricts against said elongate member resulting in a tighter seal of at least one end of said inflatable member.

8. The medical device of claim 1, wherein the decrease in diameter of one of the opposing end of said ring member restricts axial movement of said ring member.

9. The medical device of claim 1, wherein said inflatable member is a medical balloon.

10. The medical device of claim 9, wherein said medical balloon comprises ePTFE.

11. The medical device of claim 9, wherein the position of said ring member adjusts the working length of said medical balloon.

12. The medical device of claim 9, wherein said medical balloon further comprises a balloon cover.

13. The medical device of claim 12, wherein said balloon cover comprises ePTFE.

14. The medical device of claim 9, wherein said medical balloon comprises a drug coating.

15. The medical device of claim 1, wherein said ring member comprises a resilient metal.

16. The medical device of claim 15, wherein said resilient metal is nitinol.

17. The medical device of claim 1, wherein the position of said ring member adjusts the working length of said inflatable member.

18. A medical device comprising:
   an inflatable member having opposing ends, a smaller deflated profile and a larger inflated profile, and a working length; and
   a ring member having opposing ends, wherein said ring member has a position between the opposing ends of the said inflatable member and wherein an increase in diameter on one of the opposing ends of said ring member results in a compressive force in the other opposing end of said ring member;

wherein said compressive force of said one opposing end of said ring member restricts inflation of a portion of said inflatable member.

19. The medical device of claim 18, wherein the increase in the diameter of said ring member in one opposing end is driven by said inflatable member.

20. The medical device of claim 18, wherein said compressive force is caused by an increase in diameter of one of the opposing end of said ring member.

21. The medical device of claim 18, wherein said compressive force of one of said opposing end of said ring member restricts axial movement of said ring member.

22. The medical device of claim 18, wherein said inflatable member is disposed over an elongate member.

23. The medical device of claim 22, wherein said elongate member is a catheter or a guidewire.

24. The medical device of claim 22, wherein said compressive force causes said opposing end of said ring memer to constrict against said elongate member.

25. The medical device of claim 24, wherein as the diameter of said opposing end of said ring member decreases, said opposing end of said ring member further constricts against said elongate member resulting in a tighter seal of at least one end of said inflatable member.

26. The medical device of claim 18, wherein the inflatable member is a medical balloon.

27. The medical device of claim 26, wherein said medical balloon comprises ePTFE.

28. The medical device of claim 26, wherein the position of said ring member adjusts the working length of said medical balloon.

29. The medical device of claim 26, wherein said medical balloon further comprises a balloon cover.

30. The medical device of claim 29, wherein said balloon cover comprises ePTFE.

31. The medical device of claim 26, wherein said medical balloon comprises a drug coating.

32. The medical device of claim 18, wherein said ring member comprises a resilient metal.

33. The medical device of claim 32, wherein said resilient metal is nitinol.

34. A method of adjusting a working length of an inflatable member comprising:
  disposing at least one ring member onto an inflatable member having a length, wherein said at least one ring member has opposing ends and when one opposing end of said at least one ring member increases in diameter, the other opposing end of said at least one ring member decreases in diameter upon inflation of the inflatable member; and
  sliding the at least one a ring member to a predetermined position along the length of said inflatable member, wherein increasing the diameter of said one opposing ends of said at least one ring member results in a compressing force in the other posing end of said ring member.

35. The method of claim 34, wherein the increase in the diameter of said one opposing end of said at least one ring member is driven by said inflatable member.

36. The method of claim 34, wherein there are two ring members disposed on said inflatable member.

37. The method of claim 34, wherein the decrease in diameter of said one opposing end of said at least one ring member restricts inflation of a portion of said inflatable member.

38. The method of claim 34, wherein said inflatable member is disposed over an elongate member.

39. The method of claim 38, wherein said elongate member is a catheter or a guidewire.

40. The method of claim 38, wherein the decrease in diameter of the opposing end of said at least one ring member makes said opposing end constrict against the inflatable member and the elongate member.

41. The method of claim 40, wherein the constriction of the opposing end of said at least one ring member against said elongate member result in a seal of at least one end of said inflatable member.

42. The method of claim 38, wherein as the diameter of the opposing end of said at least one ring member decreases, said opposing end of said ring member further constricts against said elongate member resulting in a tighter seal of at least one end of said inflatable member.

43. The method of claim 34, wherein the decrease in diameter of one of said opposing end of said ring member restricts axial movement of said ring member.

44. The method of claim 34, wherein said inflatable member is a medical balloon.

45. The method of claim 44, wherein said medical balloon comprises ePTFE.

46. The method of claim 44, wherein said medical balloon further comprises a balloon cover.

47. The method of claim 46, wherein said balloon cover comprises ePTFE.

48. The method of claim 44, wherein said medical balloon comprises a drug coating.

49. The method of claim 34, wherein said at least one ring member comprises a resilient metal.

50. The method of claim 49, wherein said resilient metal is nitinol.

* * * * *